(12) United States Patent
Cimino

(10) Patent No.: US 6,224,565 B1
(45) Date of Patent: May 1, 2001

(54) PROTECTIVE SHEATH AND METHOD FOR ULTRASONIC PROBES

(75) Inventor: William W. Cimino, Louisville, CO (US)

(73) Assignee: Sound Surgical Technologies, LLC, Lafayette, CO (US)

( * ) Notice: Subject to any disclaimer, the term of this patent is extended or adjusted under 35 U.S.C. 154(b) by 0 days.

(21) Appl. No.: 09/191,807

(22) Filed: Nov. 13, 1998

(51) Int. Cl.$^7$ ..................................... A61B 17/20

(52) U.S. Cl. ............................ 604/22; 604/500; 604/163; 604/294

(58) Field of Search ............................. 604/22, 500, 131, 604/163, 171, 192, 198, 239, 264, 294

(56) References Cited

U.S. PATENT DOCUMENTS

| | | |
|---|---|---|
| 3,805,787 | 4/1974 | Banko . |
| 4,808,154 | 2/1989 | Freeman . |
| 4,886,491 | 12/1989 | Parisi . |
| 5,123,903 | 6/1992 | Quaid . |
| 5,236,414 | 8/1993 | Takasu . |
| 5,244,458 | 9/1993 | Takasu . |
| 5,419,761 | 5/1995 | Narayanan . |
| 5,421,829 | 6/1995 | Olichney . |
| 5,514,086 | 5/1996 | Parisi . |
| 5,527,273 | 6/1996 | Manna . |
| 5,676,649 | * 10/1997 | Boukhny et al. . |
| 5,879,356 | * 3/1999 | Geuder .................................. 604/22 |

OTHER PUBLICATIONS

Rod Rohrich, Separating Ultrasound–Assisted Lipoplasty Fact from Fiction Ultrasound–Assisted Lipoplasty Resource Guide, Plastic Surgery News, pp. 22–23,1997.

* cited by examiner

Primary Examiner—Anhtuan T. Nguyen
Assistant Examiner—Jeremy Thissell
(74) Attorney, Agent, or Firm—Dorsey & Whitney LLP

(57) ABSTRACT

In general a protective sheath for an ultrasonic fragmenting device includes a handpiece to be held and manipulated by a surgeon. The handpiece has a housing, an ultrasonic motor mounted therewithin, and an ultrasonic horn connected to the ultrasonic motor. An elongate ultrasonic probe is attached to the ultrasonic horn. The elongate ultrasonic probe has an outer surface about and along its length and has one or more vibratory nodes spaced along the length of the ultrasonic probe as a function of the resonant wavelength. The ultrasonic fragmenting device includes the protective sheath with a hollow sleeve with a proximal end and a distal end and which surrounds the elongate ultrasonic probe and extends therealong. The hollow sleeve has an inner surface formed, shaped, and sized to prevent contact with the outer surface of the elongate ultrasonic probe so that there is generally a clearance between the inner surface and the outer surface. The hollow sleeve has a connection on the proximal end to connect the hollow sleeve to the housing and a termination on the distal end located at or near the most distal vibratory node of the elongate ultrasonic probe. The termination has an inside diameter that is generally and substantially the same as the outside diameter of the elongate ultrasonic probe thereabout, and thus forms generally a barrier to the passage of material into the clearance.

15 Claims, 2 Drawing Sheets

PROTECTIVE SHEATH AND METHOD FOR ULTRASONIC PROBES

CROSS-REFERENCE TO RELATED APPLICATION

Not Applicable.

STATEMENT REGARDING FEDERALLY SPONSORED RESEARCH

Not Applicable.

REFERENCE TO A MICROFICHE APPENDIX

Not Applicable.

BACKGROUND OF THE INVENTION

This invention relates generally to surgical instruments, and, more particularly, to a surgical device for ultrasonic fragmentation or emulsification of soft tissues of a patient.

Liposuction is a surgical procedure for altering the human form, specifically by removal of localized deposits of fat tissues that are unresponsive to diet or exercise. The procedure is also known as suction lipectomy, lipolysis, and more recently as body contour surgery, body sculpting surgery, or suction-assisted liposuction. It is most often performed by plastic surgeons, although dermatologists, gynecologists, and other surgical specialties also perform such procedures.

A liposuction procedure is typically accomplished by inserting a small cannula through an incision in the skin, applying a suction source to the end of the cannula that remains outside of the body, and forcing the working end of the cannula forward and backward in the layer of fatty tissue. The fatty tissue is torn, crushed, or avulsed, and is then aspirated through small openings along the sides of the cannula near the tip and then through a central lumen in the cannula to a tissue canister placed in-line with the cannula and the suction source. The procedure may involve multiple incisions and many passes of the cannula in each incision to achieve the desired cosmetic effect for the patient. No ultrasonic energy is used in this procedure.

A liposuction cannula is typically a small metal tube with a blunt, closed end at the tip of the cannula. The blunt, closed end at the tip of the cannula is intended to minimize damage to tissues as the device is thrust forward. Small openings along the sides of the cannula near the tip create passages between the tissue and the central lumen of the cannula, which is in fluid communication with a suction source, so that tissue and fluids can be aspirated from the patient's body. In general, the suction causes the adipose tissue to be sucked into the small openings along the sides of the cannula, and the blunt dissection as provided by the surgeon's manipulation of the cannula, then tears the tissue. The fragments and released fluids are then aspirated through the openings along the sides of the cannula and then through the central lumen of the cannula.

The liposuction procedure can be traumatic for the patient. The liposuction cannula does not discriminate between adipose tissue and other tissues such as nerves, blood vessels, or lymph tissues. The mechanical disruption of those tissues by the liposuction cannula may result in, among other things, bleeding, bruising, temporary numbness, or swelling. Further, the final cosmetic result achieved for the patient is a function of the skill of the surgeon, the patient, and the type of surgical instrumentation used in the surgery. Liposuction cannulae used in the liposuction procedure may remove more adipose tissue from one area than another area in the patient, resulting in skin contour irregularities and a final cosmetic result for the patient that is not smooth or uniform or desired.

Therefore, there is a need to improve the design of liposuction cannulae to help the surgeon to better discriminate between adipose tissue and other tissues such as nerves, blood vessels, and lymph tissues, so that the adipose tissues can be fragmented and removed while the remaining tissues are damaged as little as possible or not at all. Further, there is a need to improve the design of current liposuction cannulae such that adipose tissue is removed in a uniform and predictable manner such that an improved cosmetic result is achieved for the patient.

Recently, several instruments have combined ultrasonic vibrations and the liposuction cannula to improve upon the tissue discrimination capability of the liposuction cannula and to provide an instrument, which removes adipose tissue more uniformly than current liposuction cannulae. This procedure is commonly referred to as ultrasound-assisted lipoplasty. In a typical ultrasound-assisted lipoplasty procedure, an ultrasonically vibrating cannula is inserted through an incision in the patient's skin and passed forward and backward through the adipose tissue layer. The ultrasonically vibrating cannula preferentially fragments or emulsifies the adipose tissues, which are then typically aspirated through a central lumen in the ultrasonically vibrating cannula. Consequently, the other tissues such as nerves, vessels, and lymph tissues remain generally undisturbed.

Initial experiences with the ultrasound-assisted lipoplasty procedure have been mixed. A comparison of the suction-assisted liposuction and ultrasound-assisted lipoplasty approaches with currently available surgical instruments for both procedures was recently given in *Ultrasound-Assisted Lipoplasty Resource Guide*, published in PlasticSugery News, a publication of The American Society of Plastic and Reconstructive Surgeons, 1997. In the article the author cites the disadvantages of the current ultrasound-assisted lipoplasty procedure compared to the suction-assisted liposuction procedure as: 1) burns of the skin are possible, 2) longer incisions are needed, 3) seromas are more common, 4) longer operating times, and 5) greater expense. Thus, current ultrasound-assisted lipoplasty surgical systems for fragmentation and aspiration of adipose tissues are more costly and slower than the suction-assisted liposuction procedure and have the potential to damage tissues beyond that of suction-assisted liposuction, including burns of the skin and seroma formation. There is, therefore, a need to increase patient safety, to increase the speed of the ultrasound-assisted lipoplasty procedure, and to minimize the potential for burns or seroma formation.

An ultrasonic probe for soft tissue fragmentation may be hollow, in which case the instrument may be referred to as an ultrasonic cannula or it may be solid. The distal end of an ultrasonic probe experiences small rapid excursions along an axis that passes through the proximal end and the distal end of the ultrasonic probe. A maximum excursion of 350 $\mu$m peak-to-peak at 23 kHz has been obtained in a commercially available ultrasonic aspirator for ultrasonic surgery, e.g., the CUSA of Valleylab Inc., Boulder, Colo.

An ultrasonic handpiece typically has a handle with an ultrasonic motor, an ultrasonic horn, and an ultrasonic probe. At locations along the ultrasonic probe referred to as 'vibratory nodes' the elastic stress and strain will have maximum values and there will be no motion of the ultrasonic probe relative to the handle of the ultrasonic handpiece. At locations along the ultrasonic probe referred to as 'vibratory loops' the elastic stress and strain will have minimum values and there will be maximum motion of the ultrasonic probe relative to the handle of the ultrasonic handpiece. The 'vibratory nodes' become hot as the ultrasonic probe vibrates at the resonant ultrasonic frequency because the metallic material of the ultrasonic probe is being continually worked as it is stretched and released many thousand times per second. In an ultrasound-assisted lipoplasty procedure tissue surrounds and contacts the ultrasonic probe along its length. Thus, tissue contact with a vibratory node after the probe has been in operation can cause a tissue burn. A tissue burn may also occur for any tissue that contacts a vibratory loop because of the frictional heat generated between the tissue and the rapidly moving ultrasonic probe at the vibratory loop. Further, the heat generated by the ultrasonic motor in the ultrasonic handpiece may be conducted from the ultrasonic motor through the ultrasonic horn to the ultrasonic probe, further increasing the temperature of the ultrasonic probe. The combination of these three sources of heat can and will cause tissue burns, most particularly at or near the vibratory loops.

Many patents disclose improvements and solutions for ultrasound-assisted lipoplasty instruments for removal of adipose tissue from the human body. U.S. Pat. No. 4,886,491 to Parisi has a method of removing fatty tissue from a patient using an ultrasonic probe and its energy application to melt at least some of the fatty tissue. U.S. Pat. No. 5,244,458 to Takasu has an ultrasonic handpiece with a hollow cannula with a plurality of suction openings in that cannula. U.S. Pat. No. 5,236,414 also to Takasu has an ultrasonic handpiece with a tip having a tubular body and a suction passage. U.S. Pat. No. 5,419,761 to Narayanan has an ultrasonic handpiece with a rigid tube with an axially extending lumen. U.S. Pat. No. 5,514,086 to Parisi has an ultrasonic handpiece with a probe and a tip on the probe. The tip has an acoustic impedance substantially greater than that of the probe. U.S. Pat. No. 5,527,273 to Manna has an ultrasonic lipectomy probe with an enlarged head on the distal end and a longitudinally extending channel in the probe. U.S. Pat. No. 5,123,903 to Quaid has an ultrasonic handpiece and horn, the ultrasonic horn protected by a sheath which forms an annular passage operarable to conduct fatty tissue aspirate from the distal end of the ultrasonic horn. The inner diameter of the sheath in this patent is sufficiently larger than the outer diameter of the ultrasonic horn so that the annular passage is functional for the passage of aspirated tissue and fluids, thus significantly increasing the overall diameter of the sheath. Further, the sheath terminates at the tip of the ultrasonic probe, which is a vibratory loop, thus shielding the tip of the ultrasonic probe and creating a dragging sensation for the surgeon. The end of the sheath is open and permits the flow of material into the annular passage. U.S. Pat. No. 4,808,154 to Freeman has cylindrical sleeve with at least one longitudinal rib member operable to conduct a lens flushing solution to the distal end of the ultrasonic probe. U.S. Pat. No. 3,805,787 to Banko has an ultrasonic handpiece and probe with a shield of metallic material, the shield and probe, like many of the subsequent patent efforts, are such as to be operable for the delivery of irrigation fluid to the distal end of the probe or for the removal of aspirate from the distal end of the probe. U.S. Pat. No. 5,421,829 to Olichney has an ultrasonic handpiece with a flue that surrounds a tool to direct irrigant and coolant flow thereabout.

The last four patents cited above disclose sleeves which protectively surround the ultrasonic probe, each sleeve operable for either the delivery an irrigation fluid to the distal end of the ultrasonic probe or for the removal of tissue aspirate from the distal end of the ultrasonic probe in the space created between the sleeve and the ultrasonic probe. These designs have three fundamental problems. First, when irrigation fluid or tissue aspirate is present in the space between the sleeve and the ultrasonic probe it significantly increases the power required by the ultrasonic motor to maintain a selected level of vibration amplitude due to the frictional contact between the ultrasonic probe and the irrigation fluid or tissue aspirate at the vibratory loops along the ultrasonic probe. This increased power requirement is expensive and cumbersome while causing the handle to quickly warm and become too hot to hold in a bare hand. Second, these sleeve designs terminate approximately at the distal end of the ultrasonic probe, which is a vibratory loop, and therefore have an outside diameter of the sleeve is larger than the outside diameter of the ultrasonic probe. This shielding of the ultrasonic probe makes passage of the ultrasonic probe and sleeve through the tissue difficult, creating a dragging sensation for the surgeon and generating trauma to the patient. Third, to achieve reasonable performance from either an irrigation system or an aspiration system that utilizes the space between the sleeve and the ultrasonic probe there must be sufficient clearance between the two so that resistance to flow is not too large. This increases the overall diameter of the sleeve so that a significantly larger incision is required in the patient.

While some of the patented devices have disclosed and claimed improvements and solutions to ultrasound-assisted lipoplasty instruments, none address or appreciate the needs or address the problems discussed above. Specifically none address the need for a sleeve to protect the patient from burns while minimizing the power required by the ultrasonic motor and while minimizing the diameter of the sleeve to minimize the drag in the tissue and the size of the incision in the patient.

OBJECTS OF THE INVENTION

It is, among other desirable attributes, a general object of the present invention to provide a less traumatic ultrasonic handpiece for fragmentation or emulsification of soft tissues in a patient.

It is a further object of the present invention to provide an improved ultrasonic handpiece for fragmentation or emulsification of soft tissues in a patient, which maximizes the protection of the patient from potential burns.

It is still a further object of the present invention to provide an improved ultrasonic handpiece for fragmentation or emulsification of soft tissues in the patient that maximizes the protection of the patient from burns while minimizing the forces required to pass the ultrasonic probe through the tissues.

It is yet still a further object of the present invention to provide an improved ultrasonic handpiece for fragmentation or emulsification of soft tissues in the patient that maximizes the protection of the patient from burns while minimizing size of the incision required to enter the patient.

SUMMARY OF THE INVENTION

Ultrasonic probes for fragmenting tissues of a patient are generally round in cross-section and typically have outside diameters between 1 and 5 millimeters. If a protective sheath is used to surround an ultrasonic probe it must have an inside diameter generally greater than the outside diameter of the ultrasonic probe to prevent contact therebetween. In this disclosure the clearances between the protective sheath and the ultrasonic probe are the minimum values that would generally prevent contact between the protective sheath and the ultrasonic probe, and would therefore create a clearance between the protective sheath and the ultrasonic probe that would generally be ineffective for use as a passage for irrigation or aspiration. For example, differences between the inside diameter of the protective sheath and the outside diameter of the ultrasonic probe from 0.01 to 0.50 millimeters are preferred.

In general an ultrasonic fragmenting device with a protective sheath includes a handpiece to be held and manipulated by a surgeon. The handpiece is comprised of a housing, an ultrasonic motor mounted therewithin, and an ultrasonic horn connected to the ultrasonic motor. The preferred material for the ultrasonic motor is a piezoelectric ceramic such as PZT. An elongate ultrasonic probe is attached to the ultrasonic horn. The preferred material for the ultrasonic probe is titanium or a titanium alloy. Other metallic materials may be used such as stainless steel or aluminum. The elongate ultrasonic probe has an outer surface about and along its length and has vibratory nodes spaced along its length as a function of the resonant wavelength. The ultrasonic fragmenting device includes a protective sheath that has a hollow sleeve with a proximal end and a distal end that surrounds the elongate ultrasonic probe and extends therealong. The preferred material for the hollow sleeve is thin-walled stainless steel tubing. Polymeric or plastic materials may also be used. The hollow sleeve has an inner surface formed, shaped, and sized to prevent contact with the outer surface of the elongate ultrasonic probe. The hollow sleeve has a connection on the proximal end to connect the hollow sleeve to the housing and a termination on the distal end at or near the most distal vibratory node of the elongate ultrasonic probe. In the preferred embodiment the termination has a reduced inside diameter that is generally and substantially the same as the outside diameter of the elongate ultrasonic probe thereabout, and thus forms generally a barrier to the passage of material into a minimal clearance existent between the hollow sleeve and the elongate ultrasonic probe.

In an alternative embodiment the ultrasonic probe may have a flange that circumscribes the elongate ultrasonic probe at or near its most distal vibratory node. The outside diameter of the flange is generally and substantially the same as the inside diameter of the hollow sleeve thereabout, and thus forms a barrier to the passage of material into a minimal clearance existent between the hollow sleeve and the elongate ultrasonic probe.

In yet another embodiment the clearance between the inner surface of the hollow sleeve and the outer surface of the elongate ultrasonic probe may be sufficiently small so as to effectively form a barrier to the passage of material therewithin.

Also claimed is a method of fragmenting or emulsifying a medium with axially applied ultrasonic vibrations, the method including the steps of:
surrounding an elongate ultrasonic probe with a hollow sleeve, the hollow sleeve having an inner surface formed, shaped, and sized to prevent contact with the outer surface of the elongate ultrasonic probe and;
terminating the hollow sleeve at or near the most distal vibratory node of the elongate ultrasonic probe, the termination such that the inside diameter of the hollow sleeve is generally and substantially the same as the outside diameter of the elongate ultrasonic probe thereabout for forming generally a barrier to the passage of material into a space created between the hollow sleeve and the elongate ultrasonic probe;
vibrating an elongate ultrasonic probe along its length;
engaging the medium with a distal end of the elongate ultrasonic probe, and
fragmenting or emulsifying the medium with the distal end of the elongate ultrasonic probe.

BRIEF DESCRIPTION OF THE DRAWINGS

The novel features of the invention are set forth in the appended claims. The invention will be best understood by reference to the following figure when read in conjunction with the detailed description of the invention.

DETAILED DESCRIPTION OF THE INVENTION

Figure 1:
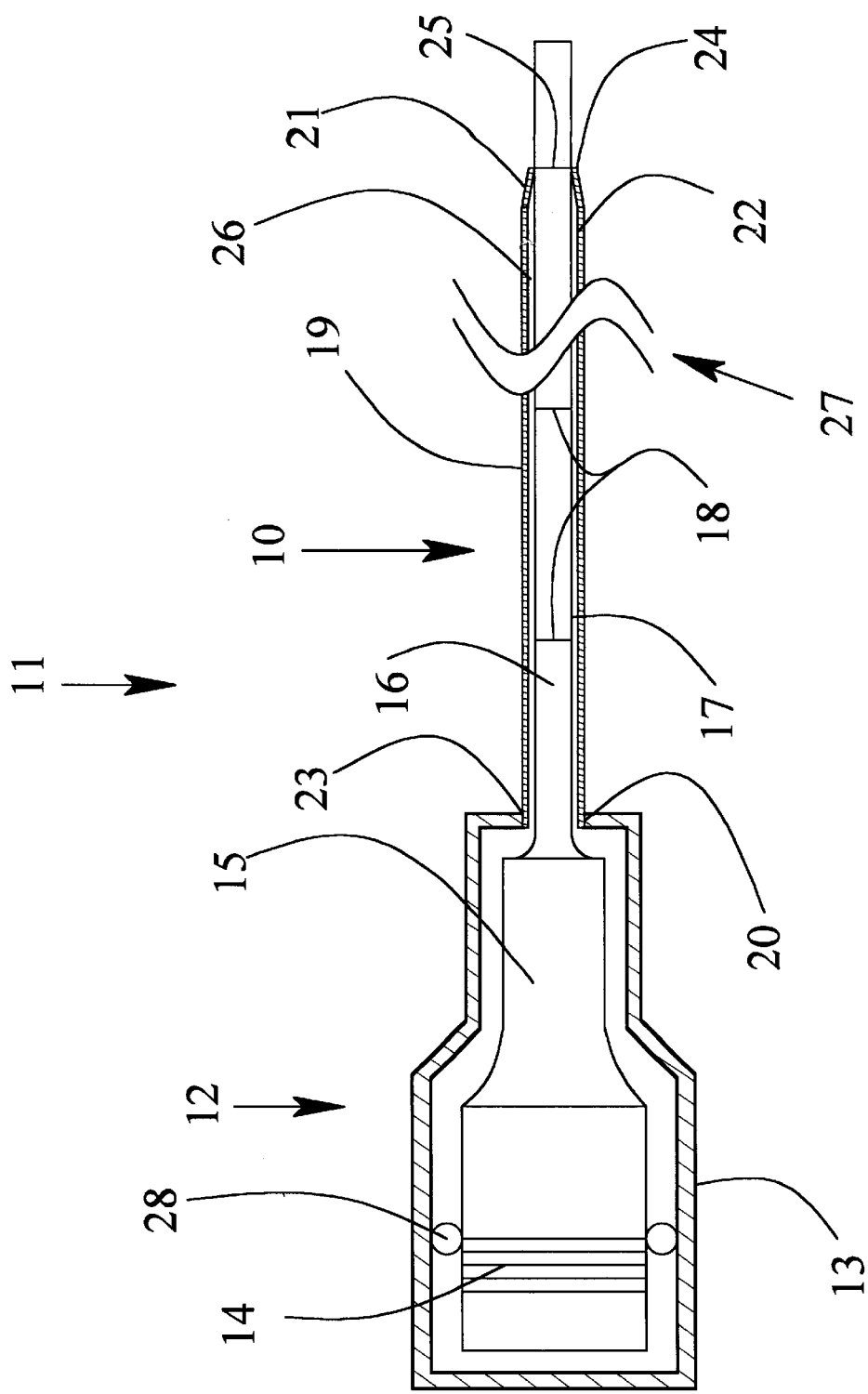
FIG. 1 is a partial cross-sectional view of an ultrasonic fragmenting device with a protective sheath terminated with a reduced inside diameter at the most distal vibratory node.

A protective sheath 10 for an ultrasonic fragmenting device 11 is shown in FIG. 1. In general the ultrasonic fragmenting device 11 includes a handpiece 12 to be held and manipulated by a surgeon, the handpiece 12 with a housing 13 and an ultrasonic motor 14 mounted therewithin. The preferred material for the ultrasonic motor is a piezoelectric ceramic such as PZT. The preferred method of mounting the ultrasonic motor 14 within the housing 13 is to suspend the ultrasonic motor 14 on O-rings 28. An ultrasonic horn 15 is connected to the ultrasonic motor 14. The preferred materials for the ultrasonic horn are aluminum alloy 7075 or titanium alloy Ti6Al4V. An elongate ultrasonic probe 16 is attached to the ultrasonic horn 15, the elongate ultrasonic probe 16 has an outer surface 17 about and along its length and vibratory nodes 18 spaced along its length as a function of the resonant wavelength. The preferred material for the elongate ultrasonic probe is titanium alloy Ti6Al4V. Other metals such as aluminum and stainless steel may also be used. Vibratory nodes 18 are depicted in FIG. 1 by lines circumscribing the elongate ultrasonic probe 16.

The protective sheath 10 has a hollow sleeve 19 with a proximal end 20 and a distal end 21 that surrounds the elongate ultrasonic probe 16 and extends therealong. The preferred material for the hollow sleeve is thin-walled stainless steel tubing. Plastic or polymeric materials may also be used. The hollow sleeve 19 has an inner surface 22 formed, shaped, and sized to prevent contact with an outer surface 17 of the elongate ultrasonic probe 16 so that there is generally a clearance 26 therebetween. The hollow sleeve 19 has a connection 23 on the proximal end 20 to connect to the housing 13. The preferred connection 23 is a snap-fit or a twist-lock between the hollow sleeve 19 and the housing 13. The connection 23 may also be accomplished using a glue joint or a molding process. The hollow sleeve 19 has a termination 24 on the distal end 21 at or near the most distal vibratory node 25 of the elongate ultrasonic probe 16. In the preferred embodiment the termination 24 has a reduced inside diameter that is generally and substantially the same as the outside diameter of the elongate ultrasonic probe 16 thereabout, forming generally a barrier to the passage of material into the clearance 26. The preferred methods of creating the reduced inside diameter at the termination 24 are tapering or swaging a metallic or polymeric tube.

The S-curves 27 shown in FIG. 1 indicate a break-in-length and are used to scale the figure so that it fits on the page. They are not part of the invention.

Figure 2:
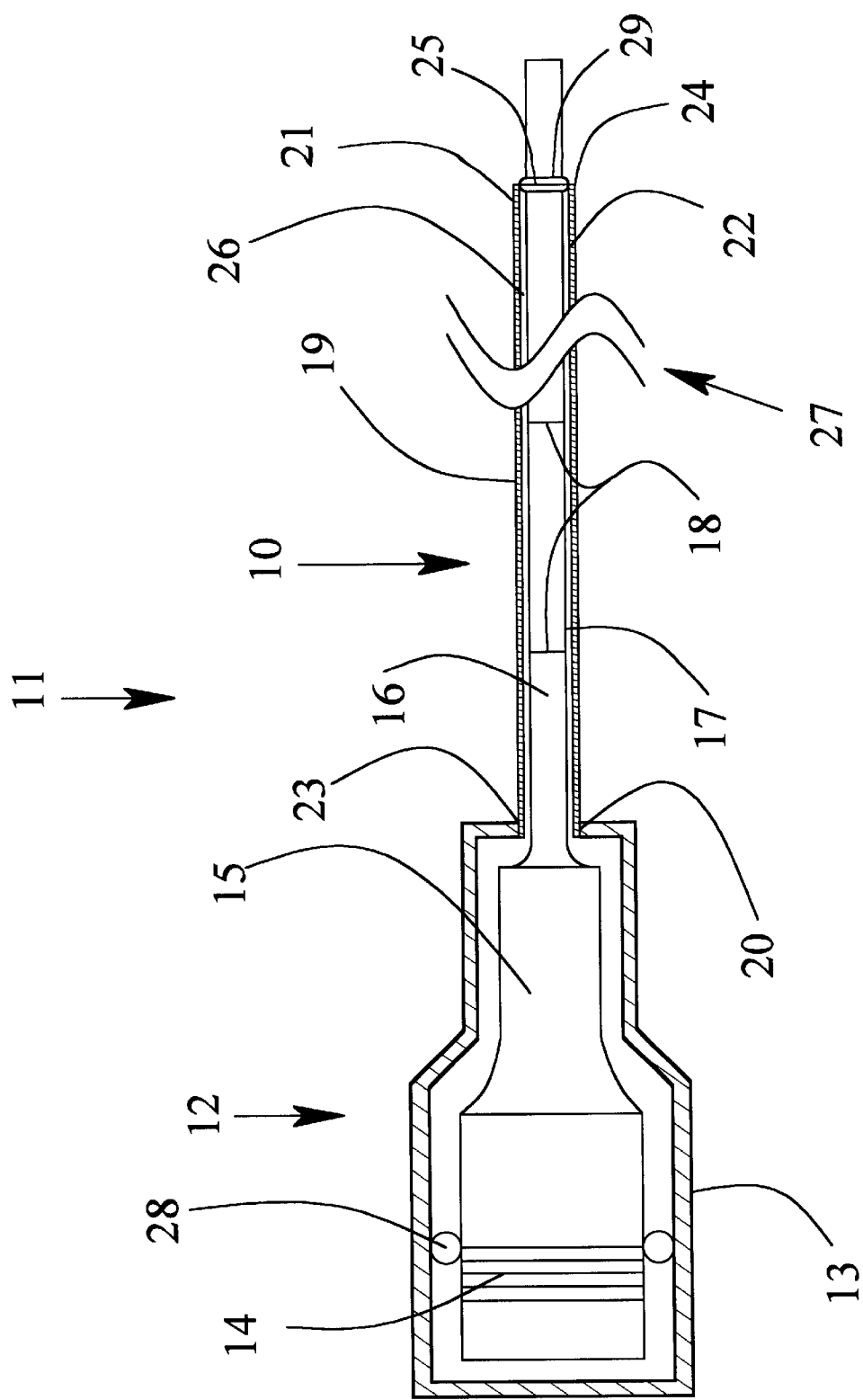
FIG. 2 is a partial cross-sectional view of an ultrasonic fragmenting device with a protective sheath terminated at a flange on the elongate ultrasonic probe at the most distal vibratory node.

An alternative embodiment of a protective sheath 10 for an ultrasonic fragmenting device 11 is shown in FIG. 2. In general the ultrasonic fragmenting device 11 includes a handpiece 12 to be held and manipulated by a surgeon, the handpiece 12 with a housing 13 and an ultrasonic motor 14 mounted therewithin. The preferred material for the ultrasonic motor is a piezoelectric ceramic such as PZT. The preferred method of mounting the ultrasonic motor 14 within the housing 13 is to suspend the ultrasonic motor 14 on O-rings 28. An ultrasonic horn 15 is connected to the ultrasonic motor 14. The preferred materials for the ultrasonic horn are aluminum alloy 7075 or titanium alloy Ti6Al4V. An elongate ultrasonic probe 16 is attached to the ultrasonic horn 15, the elongate ultrasonic probe 16 has an outer surface 17 about and along its length and vibratory nodes 18 spaced along its length as a function of the resonant wavelength. The preferred material for the elongate ultrasonic probe is titanium alloy Ti6Al4V. Other metals such as aluminum and stainless steel may also be used. Vibratory nodes 18 are depicted in FIG. 1 by lines circumscribing the elongate ultrasonic probe 16.

The protective sheath 10 has a hollow sleeve 19 with a proximal end 20 and a distal end 21 that surrounds the elongate ultrasonic probe 16 and extends therealong. The preferred material for the hollow sleeve is thin-walled stainless steel tubing. Plastic or polymeric materials may also be used. The hollow sleeve 19 has an inner surface 22 formed, shaped, and sized to prevent contact with an outer surface 17 of the elongate ultrasonic probe 16 so that there is generally a clearance 26 therebetween. The hollow sleeve 19 has a connection 23 on the proximal end 20 to connect to the housing 13. The preferred connection 23 is a snap-fit or a twist-lock between the hollow sleeve 19 and the housing 13. The connection 23 may also be accomplished using a glue joint or a molding process. The hollow sleeve 19 has a termination 24 on the distal end 21 at or near the most distal vibratory node 25 of the elongate ultrasonic probe 16. In the alternative embodiment the elongate ultrasonic probe 16 has a flange 29 that circumscribes the elongate ultrasonic probe 16 at or near the most distal vibratory node 25. The outside diameter of the flange 29 is generally and substantially the same as the inside diameter of the hollow sleeve 19 thereabout, thus forming generally a barrier to the passage of material into the clearance 26.

The S-curves 27 in FIG. 2 indicate a break-in-length and are used to scale the figure so that it fits on the page. They are not part of the invention.

What is claimed is:

1. A protective sheath and elongate ultrasonic probe for an ultrasonic fragmenting device, said device having a housing and an ultrasonic horn within and attached to said housing, comprising:

an elongate ultrasonic probe configured for attachment to the ultrasonic horn, the probe having an outer surface about and along its length and having vibratory nodes spaced along its length;

a protective sheath comprising a continuous hollow sleeve having a proximal end and a distal end, said sleeve being configured to surround the elongate ultrasonic probe and extend therealong when said sleeve and probe are aligned;

an inner surface of the hollow sleeve formed, shaped, and sized to prevent contact with the outer surface of the elongate ultrasonic probe along its length so that there is generally a clearance between the inner surface and the outer surface when said sleeve and probe are aligned;

a connection on the proximal end of the hollow sleeve to connect the hollow sleeve to the housing, and a flange of the elongate ultrasonic probe that circumscribes the elongate ultrasonic probe at or near the most distal vibratory node of the elongate ultrasonic probe when said sleeve and probe are aligned, the flange with an outside diameter that is generally and substantially the same as the inside diameter of the hollow sleeve thereabout, forming generally a barrier to the passage of material into the clearance.

2. The protective sheath of claim 1 wherein the hollow sleeve is generally metallic.

3. The protective sheath of claim 1 wherein the hollow sleeve is generally polymeric.

4. The protective sheath of claim 1 wherein the clearance between the inner surface of the hollow sleeve and the outer surface of the elongate ultrasonic probe is sufficiently small so as to effectively form a barrier to the passage of material therewithin.

5. The protective sheath of claim 4 wherein the clearance is 0.01 to 0.50 millimeters.

6. The protective sheath of claim 1 wherein the clearance flange contacts the inner surface of the sleeve.

7. A method of fragmenting or emulsifying a medium with axially applied ultrasonic vibrations, the method including the steps of:

surrounding an elongate ultrasonic probe with a continuous hollow sleeve, the hollow sleeve having an inner surface formed, shaped, and sized to prevent contact with the outer surface of the elongate ultrasonic probe along its length so that there is generally a clearance between the inner surface and the outer surface;

terminating the hollow sleeve at or near the most distal vibratory node of the elongate ultrasonic probe, the termination such that the inside diameter of the hollow sleeve is generally and substantially the same as the outside diameter of the elongate ultrasonic probe thereabout for forming generally a barrier to the passage of material into the clearance;

vibrating an elongate ultrasonic probe along its length;

engaging the medium with a distal end of the elongate ultrasonic probe, and fragmenting and/or emulsifying the medium with the distal end of the elongate ultrasonic probe.

8. The method of claim 7 wherein the medium is animal tissue.

9. The method of claim 8 wherein the medium is human tissue.

10. A method of fragmenting or emulsifying a medium with axially applied ultrasonic vibrations, the method including the steps of surrounding an elongate ultrasonic probe with a continuous hollow sleeve, the hollow sleeve having an inner surface formed, shaped, and sized to prevent contact with the outer surface of the elongate ultrasonic probe along its length so that there is generally a clearance between the inner surface and the outer surface;

providing a flange termination on the hollow sleeve at or near the most distal vibratory node of the elongate ultrasonic probe, the termination such that the inside diameter of the hollow sleeve is generally and substantially the same as the outside diameter of the elongate ultrasonic probe thereabout for forming generally a barrier to the passage of material into the clearance;

vibrating the elongate ultrasonic probe along its length;

engaging the medium with a distal end of the elongate ultrasonic probe, and fragmenting and/or emulsifying the medium with the distal end of the elongate ultrasonic probe.

11. The method of claim 10 wherein the medium is animal tissue.

12. The method of claim 11 wherein the medium is human tissue.

13. A method of fragmenting or emulsifying a medium with axially applied ultrasonic vibrations, the method including the steps of:

surrounding an elongate ultrasonic probe with a continuous hollow sleeve, the hollow sleeve having an inner surface formed, shaped, and sized to prevent contact with the outer surface of the elongate ultrasonic probe along its length so that there is generally a clearance between the inner surface and the outer surface;

sizing the clearance to generally prevent contact between the sheath and the probe but being sufficiently small that to be generally ineffective for irrigation or aspiration;

vibrating the elongate ultrasonic probe along its length;

engaging the medium with a distal end of the elongate ultrasonic probe, and fragmenting and/or emulsifying the medium with the distal end of the elongate ultrasonic probe.

14. The method of claim 13 wherein the medium is animal tissue.

15. The method of claim 14 wherein the medium is human tissue.

* * * * *